(12) United States Patent
Ding et al.

(10) Patent No.: US 10,603,047 B2
(45) Date of Patent: Mar. 31, 2020

(54) MEDICAL DEVICE FOR CUTTING BONE

(71) Applicant: MAKO Surgical Corp., Fort Lauderdale, FL (US)

(72) Inventors: Jienan Ding, Fort Lauderdale, FL (US); Xiaohui Gao, Plantation, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 401 days.

(21) Appl. No.: 15/436,460

(22) Filed: Feb. 17, 2017

(65) Prior Publication Data

US 2017/0333052 A1 Nov. 23, 2017

Related U.S. Application Data

(60) Provisional application No. 62/340,184, filed on May 23, 2016.

(51) Int. Cl.
*A61B 17/16* (2006.01)
*A61B 34/20* (2016.01)
(Continued)

(52) U.S. Cl.
CPC ........ *A61B 17/16* (2013.01); *A61B 17/00234* (2013.01); *A61B 17/1626* (2013.01); *A61B 17/1631* (2013.01); *A61B 17/1633* (2013.01); *A61B 17/1666* (2013.01); *A61B 17/1668* (2013.01); *A61B 17/1671* (2013.01); *A61B 17/32002* (2013.01); *A61B 34/20* (2016.02); *A61B 1/00163* (2013.01); *A61B 17/162* (2013.01); *A61B 17/1628* (2013.01); *A61B 17/1675* (2013.01); *A61B 90/361* (2016.02); *A61B 2017/00309* (2013.01); *A61B 2017/00323* (2013.01); *A61B 2017/00327* (2013.01); *A61B 2017/00398* (2013.01); *A61B 2017/00725* (2013.01); *A61B 2017/1602* (2013.01);
(Continued)

(58) Field of Classification Search
CPC .. A61B 17/16; A61B 17/1631; A61B 17/1642
See application file for complete search history.

(56) References Cited

U.S. PATENT DOCUMENTS 6,645,218 B1 * 11/2003 Cassidy ........... A61B 17/32002
606/170
6,656,195 B2 * 12/2003 Peters .............. A61B 17/32002
606/159
(Continued)

FOREIGN PATENT DOCUMENTS

WO WO 2009/155319 A1 12/2009

OTHER PUBLICATIONS

International Search Report and Written Opinion for International Application No. PCT/US2017/018488, dated May 3, 2017 (14 pages).

*Primary Examiner* — Nicholas W Woodall
(74) *Attorney, Agent, or Firm* — Bookoff McAndrews, PLLC

(57) ABSTRACT

A system for cutting a bone of a patient may include a motor; a rotating shaft drivingly coupled to the motor; a support tube positioned around the rotating shaft and supporting the rotating shaft at a plurality of locations; a plurality of steering wires coupled to the support tube; and a bone cutter at a distal end of the rotating shaft.

14 Claims, 6 Drawing Sheets

(51) Int. Cl.
 *A61B 17/00* (2006.01)
 *A61B 17/32* (2006.01)
 A61B 90/00 (2016.01)
 A61B 1/00 (2006.01)

(52) U.S. Cl.
 CPC ............ *A61B 2017/320032* (2013.01); *A61B 2034/2051* (2016.02); *A61B 2034/2055* (2016.02); *A61B 2034/2057* (2016.02); *A61B 2034/2061* (2016.02); *A61B 2034/2063* (2016.02); *A61B 2034/2065* (2016.02); *A61B 2090/3782* (2016.02); *A61B 2090/3966* (2016.02)

(56) References Cited

U.S. PATENT DOCUMENTS

| | | |
|---|---|---|
| 8,337,521 B2 | 12/2012 | Cooper et al. |
| 8,366,559 B2 | 2/2013 | Papenfuss et al. |
| 8,465,420 B2 * | 6/2013 | Ostrovsky .......... A61B 1/00071 600/141 |
| 8,992,421 B2 | 3/2015 | Stand et al. |
| 2005/0203527 A1 | 9/2005 | Carrison et al. |
| 2007/0093840 A1 * | 4/2007 | Pacelli ............... A61B 17/1631 606/80 |
| 2010/0057087 A1 | 3/2010 | Cha |
| 2010/0100098 A1 | 4/2010 | Norton et al. |
| 2013/0197306 A1 | 8/2013 | Armand et al. |
| 2016/0206384 A1 * | 7/2016 | Dimaio ................. A61B 34/20 |

\* cited by examiner

MEDICAL DEVICE FOR CUTTING BONE

CROSS-REFERENCE TO RELATED APPLICATION

This application claims the benefit of priority under 35 U.S.C. § 119 to U.S. Provisional Patent Application No. 62/340,184, filed May 23, 2016, the entirety of which is incorporated herein by reference.

TECHNICAL FIELD

Embodiments of the present disclosure relate generally to a medical device for cutting bone. The medical device may be flexible to access hard-to-reach surfaces, but stiff enough to cut bone.

BACKGROUND

Typically, tools used to modify bones of a patient are rigid and straight. To obtain access to certain bone surfaces using a straight tool (e.g., a cutting burr or a saw), the surgeon may have to cut a large incision through the patient's skin and tissue. For example, to carry out a knee surgery, the surgeon may have to cut a large incision through the skin to access various surfaces of the femur and tibia. Various flexible tools have been developed for procedures involving soft tissue. However, these flexible tools are not stiff enough to modify and sculpt bone in the manner required to carry out certain orthopedic procedures.

To perform orthopedic surgeries, surgeons may use tools that are part of a robotic system. The robotic system may include a computer system and other devices (e.g., components of a navigation system) to assist the surgeon in completing the medical procedure. The robotic system may help control the placement of a tool relative to the patient, for example, by tracking the patient and the tool.

SUMMARY

Embodiments of the present disclosure relate to, among other things, medical devices for cutting bone. Each of the embodiments disclosed herein may include one or more of the features described in connection with any of the other disclosed embodiments.

A system for cutting a bone of a patient may include a motor; a rotating shaft drivingly coupled to the motor; a support tube positioned around the rotating shaft and supporting the rotating shaft at a plurality of locations; a plurality of steering wires coupled to the support tube; and a bone cutter at a distal end of the rotating shaft.

The system for cutting bone may additionally or alternatively include one or more of the following features: the support tube may have stiffness of at least 5 N/mm in a bent position; the support tube may include a plurality of slots through a wall of the support tube; the support tube may include a proximal section and a distal section, and the proximal section may be independently steerable from the distal section using the plurality of steering wires; the system may include a navigation system having a detection device and a trackable element; and the navigation system may further include at least one of a fiber optic shape sensor or an electromagnetic sensor.

A medical device may include: an elongated tubular member having a wall and a lumen, wherein the elongated tubular member includes a plurality of slots extending through the wall; a flexible shaft positioned within the lumen of the elongated tubular member, wherein the flexible shaft is rotatable relative to the elongated tubular member; and a bone cutter at a distal end of the flexible shaft, wherein the elongated tubular member, in a bent position, has a stiffness of at least 5 N/mm.

The medical device may additionally or alternatively include one or more of the following features: the elongated tubular member may include a proximal section, a distal section, and a plurality of steering wires, and the proximal section may be independently steerable from the distal section; the distal section may be steerable by at least four steering wires, with each steering wire including a first section extending along a length of the proximal section and along a length of the distal section and a second section extending along the length of the proximal section and along the length of the distal section, and the proximal section may be steerable by at least four additional steering wires, with each of the four additional steering wires including a first section extending along the length of the proximal section and a second section extending along the length of the proximal section; the medical device may include an enclosed lumen; and the flexible shaft may be configured to rotate at a speed of at least 10,000 rpm.

A method for cutting a bone of a patient may include: placing a bone cutter adjacent to the bone, wherein the bone cutter is positioned at a distal end of a rotating shaft, and a support tube is positioned exterior to the rotating shaft; modifying a shape of the support tube by at least one of increasing a curvature or decreasing the curvature of at least a portion of the support tube; and rotating the flexible shaft to cut the bone.

The method for cutting bone may additionally or alternatively include one or more of the following features or steps: the support tube may include a first section and a second section, and the first section may be configured to bend in any direction relative to a straight position of the first section, and the second section may be configured to bend in any direction relative to a straight position of the second section; the method may further comprise tracking a position of the bone cutter relative to the bone using a navigation system; the navigation system may include at least one of a fluoroscope, an ultrasound device, a fiber optic shape sensor, or an electromagnetic sensor; the navigation system may include a camera and a trackable element; modifying a shape of the support tube may include applying tension to at least one steering wire; the support tube may support the rotating flexible shaft at a plurality of locations; the flexible shaft may be drivingly coupled to a motor, and rotating the flexible shaft may include rotating a portion of the motor; and the method may further comprise calibrating a computer model of the support tube.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Medical Device Components

The present disclosure is drawn to medical devices for cutting bone. The medical device may be hand-held or may be an end effector coupled to a robotic device. The medical device may be flexible, which may allow it to access and modify various surfaces of a bone during a minimally-invasive surgery. Although flexible, the medical device may be stiff enough to allow it to maintain its bent shape while cutting hard surfaces such as bone. A computer system and a navigation system may aid in controlling the shape and positioning of the medical device and may provide image guidance to a user.

Figure 1:
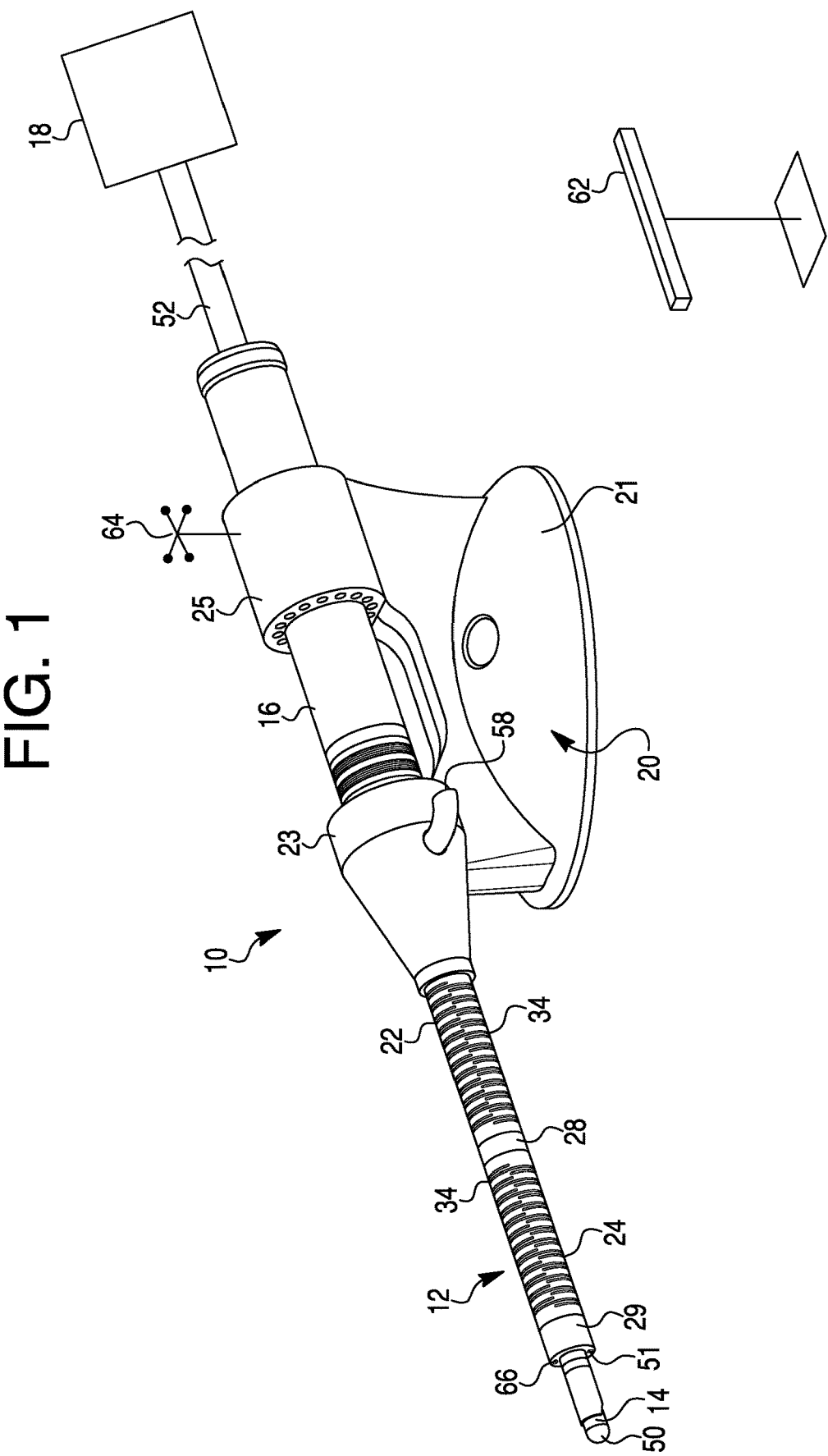
FIG. 1 illustrates a medical device for cutting bone in accordance with the present disclosure.

Referring to FIG. 1, the medical device 10 may include, among other components, a flexible tubular member 12, an inner shaft 14, a first motor 16, a second motor 18, and a housing 20.

The flexible tubular member 12 may include a proximal section 22 and a distal section 24 that are each separately controllable. In an alternative embodiment, the flexible tubular member 12 does not include separate sections 22, 24 but instead is a single tubular member with any of the characteristics described herein in connection with the proximal and distal sections 22, 24. The proximal and distal sections 22, 24 may include any suitable material, such as metals or polymers. In one example, the proximal and distal sections 22, 24 may include shape memory material, such as nitinol or spring steel. Together, the proximal and distal sections 22, 24 may define a lumen 26 that holds the inner shaft 14. The walls of the proximal and distal sections 22, 24 may have any suitable thickness, and in various examples may include a thickness between 0.2-5 mm, 1-4 mm, or 1.5-3 mm. In one example, the wall thickness may be about 1.75 mm.

The tubular member 12 may further include one or more connectors 27, 28, 29 (also see FIG. 2) to connect the proximal and distal sections 22, 24 to other components and to each other. The connectors may have a rigid, tubular shape. However, in an additional or alternative embodiment, one or more connectors 27, 28, 29 may be rigid and curved. Curved connectors may be useful to access certain portions of a patient's anatomy with the medical device 10. In one embodiment, connectors may be interchangeable to modify the shape of the tubular member 12 for different procedures. For example, different connectors may have different lengths and/or curvatures.

Each of the proximal and distal sections 22, 24 may include a plurality of slots 34. The slots 34 may extend partially or fully through the wall of the corresponding section 22, 24. Each slot 34 may be elongated, with its longer sides parallel to each other and extending at least partially around the circumference of the corresponding section 22, 24. The ends of each slot 34 may be straight or curved.

Furthermore, in one example, each slot 34 may extend about 270 degrees around the circumference of the corresponding section 22, 24. In other examples, each slot 34 may extend between 180 degrees and 330 degrees around the circumference of the corresponding section 22, 24, although each slot 34 may extend any suitable number of degrees around the circumference. In an additional or alternative example, two or more distinct slots may lie on the same circumference of the corresponding section 22, 24 at a certain longitudinal location, and material may be left between the ends of the slots to prevent the section from breaking apart (e.g., two 120° slots around a circumference, with 60° of material between the ends of the two slots).

Figure 4:
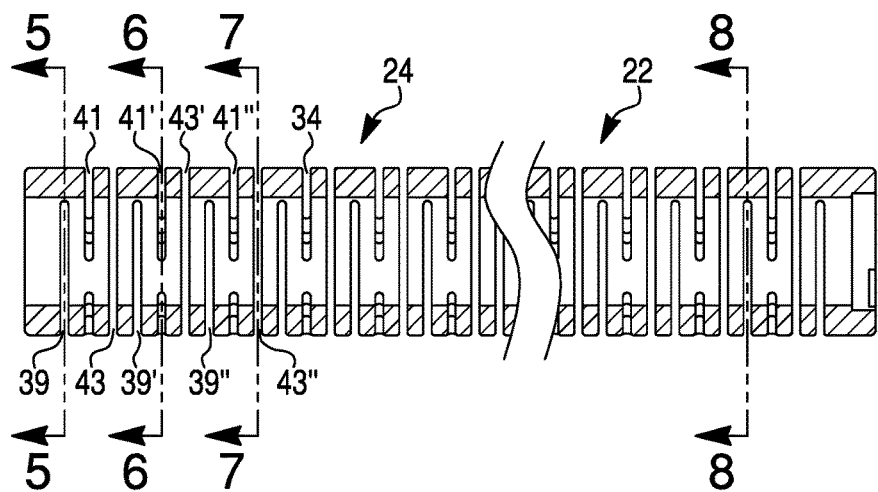
FIG. 4 illustrates a longitudinal, cross-sectional view of portions of the proximal and distal sections of the flexible tubular member of the medical device of FIG. 1.

FIG. 4 illustrates portions of the proximal and distal sections 22, 24 of FIG. 1, along with representative cross-sections of these sections. As shown in FIGS. 5-8, control wires 30 may travel through the walls of the proximal and distal sections 22, 24 to allow a user to control the position of the cutting tool 50 at the distal end of the inner shaft 14. For ease of reference, the inner shaft 14 is not shown in FIGS. 4-8.

Referring to FIG. 4, slots 34 may be arranged in a three-slot pattern, with every third slot being positioned in a similar orientation. For example, travelling along the length of a tubular member 22, 24, a first set of slots may include a first slot 39, a second slot 41, and a third slot 43. After the third slot of the first set, a second set of slots may include a first slot 39', a second slot 41', and a third slot 43'. A representative first slot 39 of the distal section 24 lies on cross-section 5-5, a representative second slot 41 lies on cross-section 6-6, and a representative third slot 43 lies on cross-section 7-7. The first slots of each set may be oriented similarly to each other, the second slots of each set may be oriented similarly to each other, and the third slots of each set may be oriented similarly to each other. Furthermore, adjacent slots 34 may be arranged such that each slot is turned 120 degrees with respect to adjacent slots, as shown in the cross-sections 5-5, 6-6, and 7-7.

Figure 8:
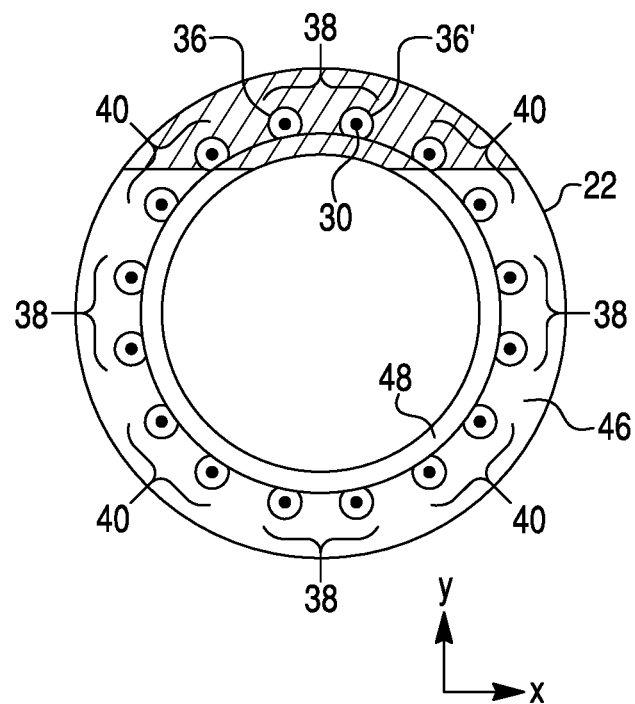
FIG. 8 illustrates a transverse, cross-sectional view at section 8-8 of FIG. 4.

FIG. 8 illustrates an exemplary slot through the proximal section 22, along cross-section 8-8 of FIG. 4. The slots of proximal section 22 may have the same configuration and pattern as the slots of FIG. 4. Referring to FIG. 8, the illustrated slot may have the same orientation as the slot of cross-section 5-5.

As can be seen in the cross-sections of FIGS. 4-8, an individual slot 34 may pass through portions of the wall of the tubular member 12, leaving a segment of the wall intact. Because each slot may be rotated 120 degrees with respect to adjacent slots, adjacent segments may be rotated 120 degrees with respect to each other. Accordingly, travelling along the length of the tubular member 12, the segments of remaining wall material may form a spiral configuration.

Figure 9:
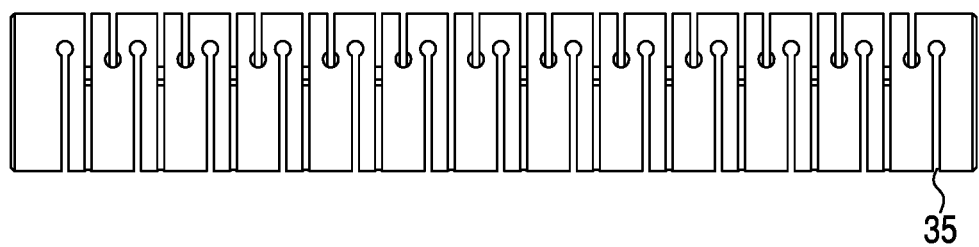
FIG. 9 illustrates an exemplary embodiment of a slot configuration of a flexible tubular member.
Figure 10:
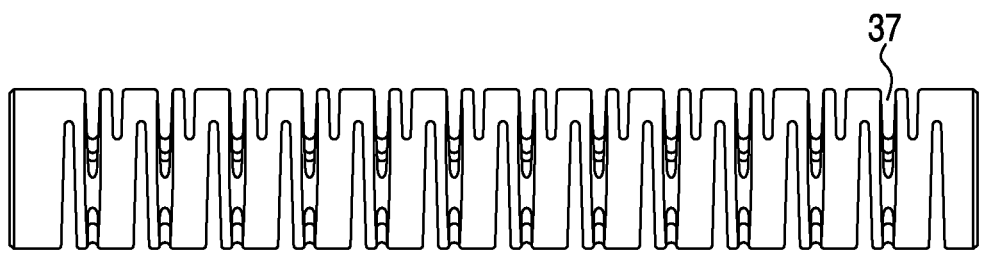
FIG. 10 illustrates another exemplary embodiment of a slot configuration of a flexible tubular member.

Additional or alternative slot configurations are shown in FIGS. 9 and 10. Referring to FIG. 9, the slots 35 may include expanded ends. The expanded ends may relieve stress on tubular member 12 and may increase the bending angles of the tubular member 12. Referring to FIG. 10, each slot 37 may be tapered towards its ends, such that a middle portion of each slot is wider than its end portions. The various slot configurations may alter the flexibility of the tubular member 12. For example, the slots 37 having wider middle regions may increase the flexibility of the tubular member. The slots 35, 37 of FIGS. 6 and 7 may include any other features described in connection with slots 34, including their length around the circumference of the tubular member 12 and their orientation relative to adjacent slots.

The slots 34 may allow the flexible tubular member 12 to bend, even if the material of the proximal and distal sections 22, 24 is relatively rigid. Furthermore, because the slots 34 are distributed around the circumference of the tubular walls, each of the proximal and distal sections 22, 24 is configured to bend in any direction.

Figure 5:
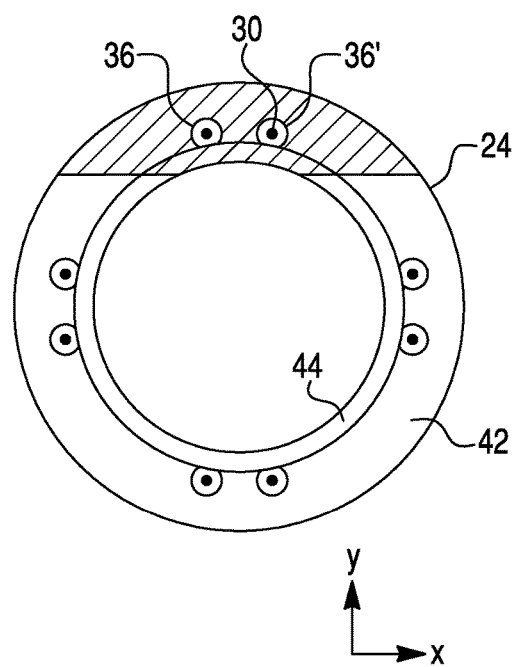
FIG. 5 illustrates a transverse, cross-sectional view at section 5-5 of FIG. 4.
Figure 6:
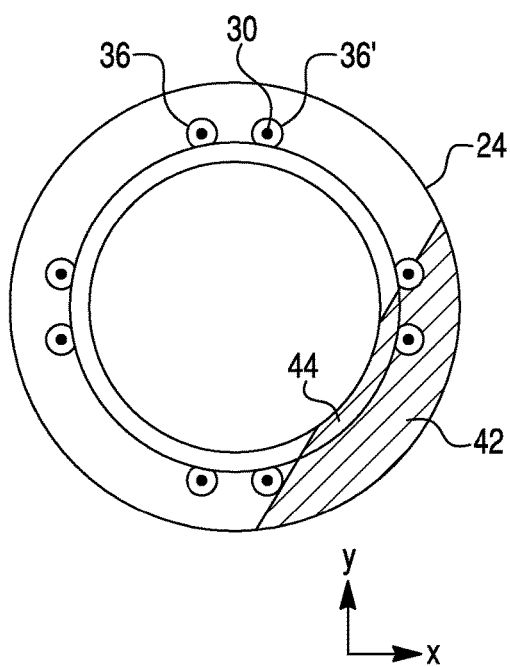
FIG. 6 illustrates a transverse, cross-sectional view at section 6-6 of FIG. 4.
Figure 7:
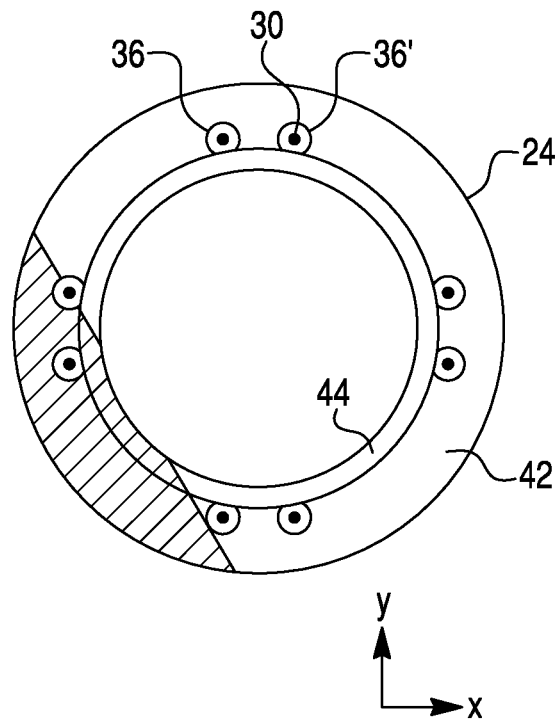
FIG. 7 illustrates a transverse, cross-sectional view at section 7-7 of FIG. 4.

Referring to FIGS. 5-7, the distal section 24 may include a plurality of control wire openings 36 to hold control wires 30. The control wire openings 36 may be grouped in pairs, such as openings 36 and 36'. A pair of openings 36 and 36' may hold the same control wire 30, with the control wire 30 extending through one of the openings 36, 36', bending near the distal end of the distal section 24 to form a "U-turn," and extending through the other of the openings 36, 36'. Accordingly, a first portion of the control wire 30 may be positioned in a first opening 36 of a pair and a second portion of the control wire may be positioned in second opening 36' of the pair. In one example, each of the control wires 30 may U-turn at the distal end of the distal section 24. However, in an alternative example (see exploded view of FIG. 2), the y-direction control wires 30 (the top and bottom control wires in FIG. 4) may travel through the connector 29 positioned distal to the distal section 24 and may U-turn at the distal end of the connector 29, while the x-direction control wires 30 (the left and right control wires in FIG. 4) may U-turn at the distal end of distal section 24.

The remaining pairs of openings shown in FIG. 4 may similarly hold first and second portions of other control wires 30. In the example shown, four control wires 30, which run through a total of eight control wire openings 36, 36', may control movement of the distal section 24. However, in other embodiments, one, two, three, or five or more control wires may control movement of the distal section 24.

The configuration of control wires 30 through the distal section 24 may allow a user to control the shape of distal section 24. As noted above, two of the control wires 30 may control movement of the distal end of distal section 24 in the x-direction and two of the control wires 30 may control movement of the distal end of distal section 24 in the y-direction. The four control wires of the embodiment in FIG. 4 can therefore be used to bend the distal section 24 along both the x-axis and y-axis. For example, shortening one control wire 30 (e.g., an x-direction control wire) and lengthening the opposite control wire 30 (e.g., the other x-direction control wire) may bend the distal section 24 towards the shortened side. Tightening more than one control wire 30 (e.g., one x-direction control wire and one y-direction control wire) and lengthening the other two opposite control wires 30 (e.g., the other x-direction control wire and the other y-direction control wire) may bend the distal section 24 partially along the x-axis and partially along the y-axis.

Accordingly, the distal section 24 may be controlled in a manner that allows the distal end of the distal section 24 to move in any direction. Bending the distal section 24 may increase the curvature of at least a portion of the distal section 24, and bringing the distal section 24 back towards a straight position may decrease the curvature of at least a portion of the distal section 24. As the distal section 24 bends farther and approaches 90 degrees, the distal end moves proximally in the z-direction, in additional to its movement in the x and y directions. The "working area" of the cutting tool 50, based only on movement of the distal section 24, may therefore be the outer boundary of a semi-spherical shape.

Referring to FIG. 8, the wall of proximal section 22 of the flexible tubular member 12 may also include control wire openings 36, 36' holding control wires 30. For ease of reference, each distal section control wire and its corresponding openings are collectively referred to as a distal control 38, and each proximal section control wire and its corresponding openings are collectively referred to as a proximal control 40. The components of the proximal controls 40 may be similar to the components of the distal controls 38 described above (e.g., control wires 30 through openings 36, 36') and may function in a similar manner to control the proximal section 22. In the example shown, four proximal controls 40, including four control wires 30 running through a total of eight control wire openings 36, 36', control movement of the proximal section 22 as described above in connection with the distal section 24. However, in other embodiments, one, two, three, or five or more control wires may control movement of the proximal section 22. The working area of the cutting tool 50, based only on movement of the proximal section 22, may also be the outer boundary of a semi-spherical shape. The ranges of motion provided by each of the proximal and distal sections 22, 24 may combine to increase the number of positions of the cutting tool 50 that are achievable without repositioning the housing 20 of the medical device 10. Furthermore, as described below, the medical device 10 may be fixed to a robotic arm of another device, which may provide additional degrees of freedom for positioning the cutting tool 50.

Figure 2:
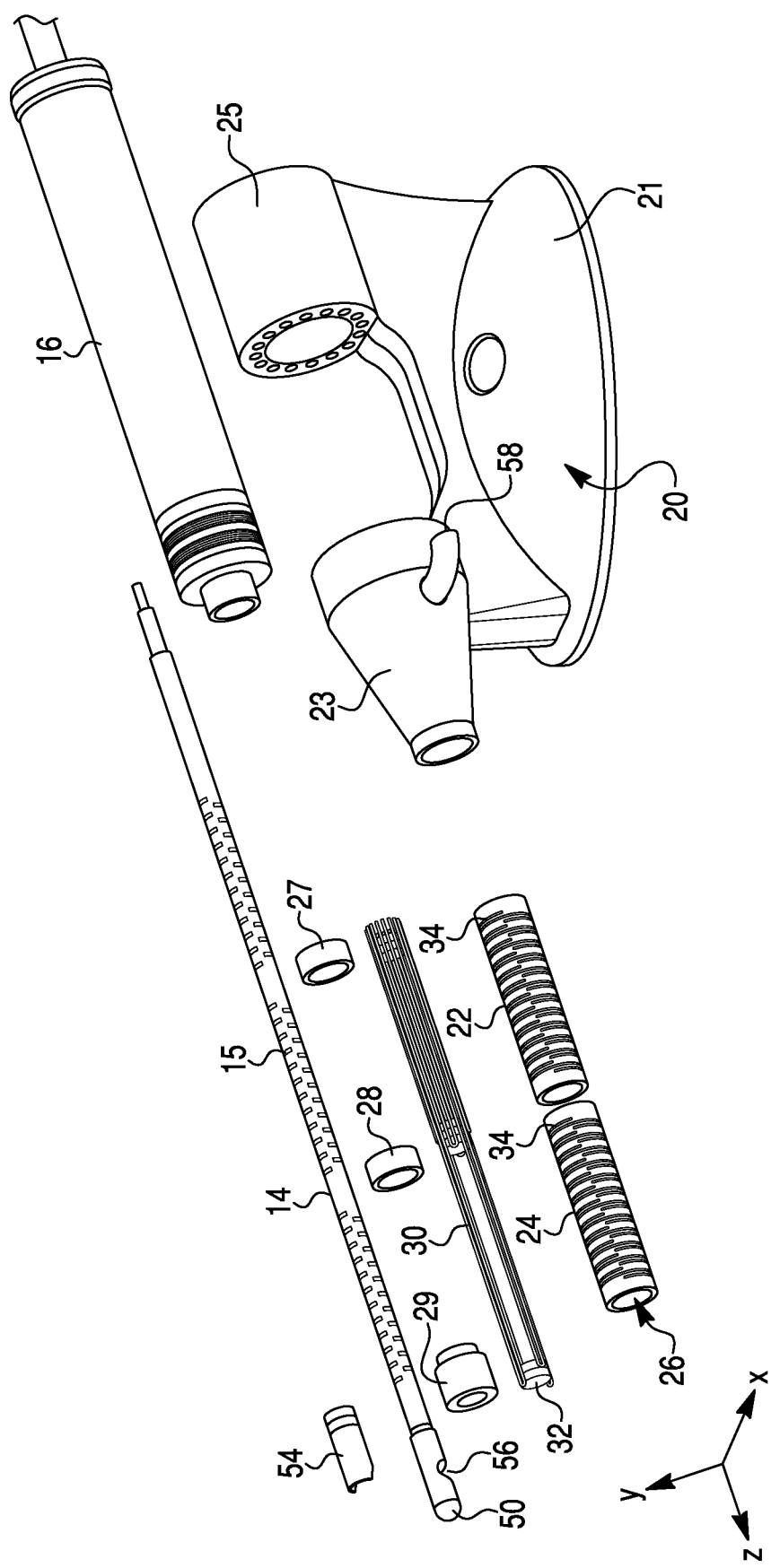
FIG. 2 illustrates an exploded view of the medical device of FIG. 1.

The distal controls 38 may travel proximally from the distal section 24 and through the proximal section 22, as shown in FIG. 8. Within the proximal section 22, the components of the proximal controls 40 may be positioned between the components of the distal controls 38. Similarly to the distal controls 38, the proximal controls 40 may allow the user to bend the proximal section 22 in any direction along the x and y axes. In total, sixteen control wire openings 36, 36' may travel through the wall of the proximal section 22. Also similar to the distal control wires 30, the proximal control wires 30 may "U-turn" near the distal end of the proximal section 22. In one example, each of the four control wires U-turns at the distal end of the proximal section 22. In an alternative example, as shown in FIG. 2, two of the control wires 30 may travel through the connector 28 positioned between the proximal and distal sections 22, 24 and may U-turn at the distal end of the connector 28, while the other two control wires 30 may U-turn at the distal end of the proximal section 22.

The control wires and their corresponding openings 36, 36' may allow each section 22, 24 of the flexible tubular member 12 to bend up to 90 degrees in any direction. Each section 22, 24 may be independently controllable or steerable using the control wires 30. This flexibility may allow the user to precisely position the distal end of the medical device 10. Specifically, the distal end of each section of the flexible tubular member 12 can trace a full 360 degree circle around a longitudinal axis defined by the section in a straight configuration. Stated in other words, relative to a fixed reference axis traveling through the proximal and distal ends of a section in a straight configuration, and without having to turn the whole section 22, 24, each section can be bent to move the distal end of each section radially outward in any direction.

Although the tubular member 12 is flexible, it may be able to resist unintentional bending while the user is cutting bone.

Accordingly, the tubular member 12 may be configured to change shapes at certain times and to maintain its shape at certain times. In contrast, a rigid tool that is not meant to change shapes must only have sufficient rigidity so that it will not break or deform during cutting of bone. The control wires 30 may provide sufficient stiffness to the sections 22, 24 of the tubular member 12, which may allow the tubular member 12 to cut bone without unintentional flexing.

The inclusion of eight control wire lengths (e.g., with each control wire 30 including two lengths) along a cross section of the distal section 24 and sixteen control wire lengths along a cross section of the proximal section 22 may be useful in allowing the tubular member 12 to maintain a desired shape, even when cutting or otherwise modifying hard structures such as bone. In other examples, a different number of control wire lengths along the proximal or distal section 22, 24 may provide a sufficient stiffness. Accordingly, high forces may be exerted by the distal end of the medical device 10 without compromising the intended shape of the proximal and distal sections 22, 24 as positioned by the control wires 30. In one embodiment, the tubular member 12 may have a stiffness of at least 5 N/mm. In other embodiments, the stiffness of the tubular member 12 may be at least 5.5 N/mm, 6 N/mm, 6.5 N/mm, or 7 N/mm. The stiffness of the tubular member 12 may be measured by applying an external force at an end of the tubular member 12, then measuring the resulting end deflection. The stiffness may then be calculated by dividing the applied force by the deflection. In one embodiment, the flexible shaft 14 does not affect the stiffness of the tubular member 12, although in other embodiments the flexible shaft 14 may increase the stiffness of the tubular member 12.

The stiffness of the tubular member 12 may also be influenced by other factors, such as the thickness and arrangement of the control wires 30, the material of the tubular member 12, and the number and shape of slots 34 in the walls of the tubular member 12. For example, the proximal and distal sections 22 may include high-strength Nitinol, which may be stronger and softer than other materials and may allow the tubular member 12 to withstand high forces without unintentional bending. Additionally, the arrangement of the control wires 30, which may each include a "U-turn" near the distal end of a corresponding section 22, 24, may save room and allow additional lengths of wire to pass through the wall of the tubular member 12 because the clamping mechanisms for securing the wires can be placed outside of the tubular member at its proximal end, rather than at the working distal end. The additional wires may increase the stiffness of the tubular member 12. Prior art flexible devices that do not have a sufficient stiffness may unintentionally bend if used to cut harder surfaces, which may make them unsuitable for cutting bone.

The control wires 30 of both proximal and distal sections 22, 24 may be controlled by one or more motors 18, shown schematically in FIG. 1. The control wires 30 may travel proximally through housing 20 and/or a lumen within motor 16 and through a lumen 52 to motor 18. In one example, the motor 18 may include one or more tension screws. The two proximal ends of each control wire 30 may be wrapped around or otherwise coupled to a corresponding tension screw. The tension screws may be rotated to shorten or lengthen control wires 30, causing the flexible tubular member 12 to bend.

In one example, the proximal ends of a first control wire and the proximal ends of a second control wire positioned opposite the first control wire may be coupled to the same tension screw. Therefore, when the screw turns, one control wire shortens and the other lengthens to bend a section of the flexible tubular member 12. Controlling the wires of a single section may therefore require two motors—one motor for each pair of control wires. In an alternative example, three control wires that form a triangular pattern may be used to control each section of the tubular member 12. In this example, three motors may be used—one for each control wire. An encoder may be used to measure the rotation of the tension screws. The motor 18 may be located close to the remaining components of the medical device 10 or may be located in a remote location, with the control wires 30 traveling from the motor 18 to the proximal and distal sections 22, 24. Bowden cables may be used to transmit motion from a remote motor to the control wires 30. In an additional or alternative example, the control wires 30 may be controlled by a hydraulic or pneumatic piston. For example, the motor may cause movement of pistons, which in turn may pull on or release tension from one or more control wires 30. In yet another example, the proximal and distal sections 22, 24 of the flexible tubular member 12 may be controlled by a shape memory material, such as nitinol or spring steel. In this example, the shape memory material (e.g., in the shape of an elongated member) may be coupled to one or more control wires. The shape memory material may then be activated by an electrical current to either pull on or release tension from one or more control wires 30.

In an alternative example, each control wire 30 may pass through only one opening 36. In this example, the distal ends of control wires 30 of distal controls 38 may be secured to the distal end of distal section 24. Similarly, the distal ends of control wires 30 of proximal controls 40 may be secured to the distal end of proximal section 22.

The openings 36, 36' through the wall of both the proximal and distal sections 22, 24 may be formed by any suitable method, such as drilling the openings through the wall. However, referring to FIGS. 5-8, in one example, the distal section 24 may include an outer tube 42 and an inner tube 44, and the proximal section 22 may include an outer tube 46 and an inner tube 48. Before assembly with the inner tubes, slots may be formed in an inner wall of the outer tubes of each section 22, 24 to form the openings 36, 36'. Each inner tube may then be placed inside of the lumen of the corresponding outer tube so that the exterior of the inner tube forms the inner wall of the openings 36, 36'. The inner and outer tubes of each section may be made of the same material or of different materials. This method for forming the openings 36, 36' may reduce the cost of manufacturing the control wire openings 36, 36'.

Referring to FIG. 1, the medical device 10 may include an imaging device 51 near its distal end (e.g., in the vicinity of cutting tool 50, described below) to facilitate intraoperative imaging. For example, an ultrasound probe or a video camera may be secured to the distal end of distal section 24, which may be useful to visualize the patient's anatomy. In an additional or alternative embodiment, the imaging device 51 may be a camera located at a distal end of an endoscope. The endoscope may travel through an opening in the wall of the tubular member 12, with any electrical or data transmitting wires traveling proximally through the opening. The medical device 10 may include a mechanism for protecting the imaging system from blood or tissue, such as a cover, or may include a feature to direct irrigation liquid towards the surface of the probe or camera for cleaning and visibility purposes.

Referring to FIGS. 1 and 2, the medical device may further include a flexible shaft 14 positioned within the lumen 26 of the flexible tubular member 12. The flexible shaft 14 may include a cutting tool 50 at its distal end. The flexible shaft 14 may have a hollow interior and may include slots 15 that extend partially or fully through the wall of the flexible shaft 14. The slots 15 may extend along sections of the flexible shaft 14 that align with proximal and distal sections 22, 24 of the tubular member 12. The slots 15 may further facilitate bending of the flexible shaft 14 when the tubular member 12 is bent using the control wires 30. The slots 15 may be aligned in two or more rows extending parallel to a longitudinal axis of the flexible shaft 14. The slots may be elongated around the circumference of the flexible shaft 14 and may have a substantially rectangular shape, although the slots 15 may have any shape.

In an alternative example, the flexible shaft 14 may be the flexible drive shaft described in U.S. Pat. No. 8,366,559, titled "Cannulated Flexible Drive Shaft," issued Feb. 5, 2013, and hereby incorporated by reference herein in its entirety. Accordingly, the flexible drive shaft may include a plurality of interlocking sections or rings, with protruding pins from one section fitting into sockets of adjacent sections. In one example, the flexible shaft 14 may transmit minimal or zero bending moment. In an alternative embodiment, the flexible shaft 14 may include a torque coil. Any embodiment of a flexible shaft 14 may additionally or alternatively include force and/or torque sensors to improve accuracy. The computer system, described further below, may reposition or stop cutting based on the detected force and/or torque. In one example, if the monitored force or torque exceeds a certain limit, the computer system may indicate an unacceptable change in the position of cutting tool 50 and may stop rotation of the cutting tool 50.

The flexible shaft 14 may rotate at speeds sufficient to cut bone. In one example, the flexible shaft 14 may rotate at a speed of at least 10,000 rotations per minute. In other examples, the flexible shaft 14 may rotate at speeds of at least 20,000, 30,000, 40,000, 50,000, or 60,000 rotations per minute while retaining its ability to bend along with the proximal and distal sections 22, 24. The flexible shaft 14 may be powered by a motor 16, shown in FIG. 1. The motor 16 may be an elongated cylindrical shape and may be held by the housing 20. The motor 16 may be coupled to a source of power via one or more electrical cables.

The distal end of the flexible shaft 14 may include a cutting tool 50 that rotates to cut or sculpt bone or other portions of a patient's anatomy. The cutting tool 50 may be rigidly fixed to the flexible shaft 14. In one example, the cutting tool 50 may be a burr that includes a rounded distal end. In other examples, the distal end of flexible shaft 14 may include a different cutting tool 50, such as a blade or drill. The cutting tool 50 may be at least partially surrounded by a collar 54. The collar 54 may prevent certain portions of the cutting tool 50 from contacting tissue, allowing the user to cut only tissue adjacent to the exposed portions of cutting tool 50.

Figure 3:
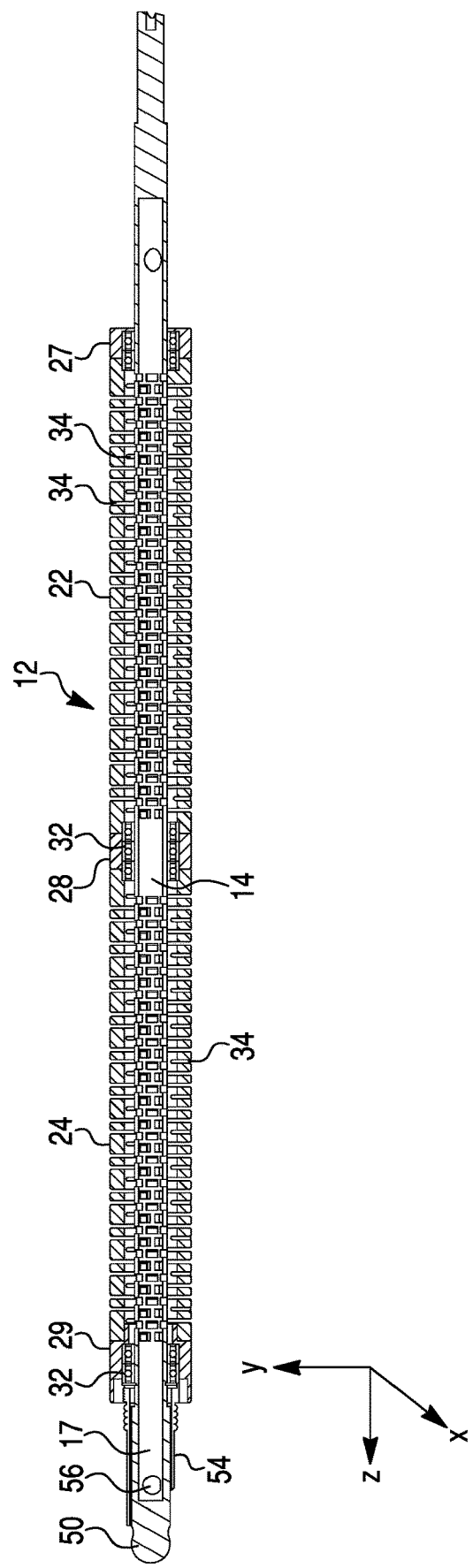
FIG. 3 illustrates a longitudinal, cross-sectional view of the flexible tubular member of the medical device of FIG. 1.

Referring to FIGS. 1, 2, and 3, the interior of the tubular member 12 may include an enclosed lumen 17 that is exposed to the exterior of the tubular member 12 only through a proximal port 58 and a distal port 56. The enclosed lumen 17 may be defined by an elongated flexible tube that travels through the interior or exterior of the flexible shaft 14. The flexible tube may include polymers or other flexible material that can rotate and bend in conjunction with the tubular member 12 and flexible shaft 14. The enclosed lumen 17 may allow a user to withdraw tissue, bone, and blood from the body of the patient through distal port 56 as the cutting tool 50 is used to cut bone. A vacuum or other suction source may be coupled to the proximal port 58.

Additionally or alternatively, water or other fluid may be injected through the proximal port 58, through the enclosed lumen 17, and out of distal port 56 to irrigate the surface of the bone. Both the suction and irrigation functions may increase visibility of the working area during a medical procedure. A tubular member may be used to connect proximal port 58 to a vacuum source and collection chamber to collect suctioned material or to a source of fluid for irrigating.

As noted above, the flexible shaft 14 and each section 22, 24 of the flexible tubular member 12 may be flexible. In one example, flexible means that a component is configured to bend at least 5° relative to a straight line along the longitudinal axis of the component in a straight position. For example, with the flexible shaft 14 starting in a straight position and defining a straight line extending along the longitudinal axis of the flexible shaft 14, and with the proximal end of the flexible shaft 14 remaining on the straight line, the distal end of the flexible shaft 14 may be able to bend at least 5° away from the straight line. In other examples, a flexible component may be configured to bend at least 10° relative to a straight line, at least 15°, at least 20°, at least 25°, at least 30°, at least 35°, at least 40°, at least 45°, at least 50°, at least 55°, at least 60°, at least 65°, at least 70°, at least 75°, at least 80°, at least 85°, or at least 90°.

Referring to FIG. 3, bearings 32 may lie between the tubular member 12 and the inner flexible shaft 14 to facilitate rotation of the inner flexible shaft 14 relative to the tubular member 12 and other components of the medical device. For clarity, the cross section of FIG. 3 is taken at a location that does not intersect control wires 30 or control wire openings 36, 36'. Furthermore, the wall of tubular member 12 is shown as one material, although as described in connection with FIGS. 4 and 5, the wall of the tubular member 12 may include two different materials or tubular members coupled together. The bearings 32 may lie exterior to the flexible shaft 14 and interior to the connectors 27, 28, 29. The inner flexible shaft 14 may include smooth sections, as shown in FIG. 2, to facilitate coupling of the bearings 32. Similarly, the interior of the connectors may be smooth to facilitate coupling of the bearings 32 to the tubular member 12. The bearings 32 may allow the tubular member 12 to act as a support tube that supports the rotating flexible shaft 14 at a plurality of locations. For example, the bearings 32 may be useful in preventing the flexible shaft 14 from buckling within the tubular member 12 when forces are exerted on cutting tool 50.

Referring to FIG. 1, the medical device 10 may further include a housing 20. The housing may support components of the medical device with two supports 23, 25. The supports may protrude from a base 21. Each support 23, 25 may include a lumen for receiving other components of the medical device 10. In one example, support 23 may receive the proximal end of tubular member 12 and a portion of motor 16, and support 25 may receive a proximal portion of motor 16. When the medical device 10 is used as an end effector with a robotic arm, housing 20 may secure the medical device 10 relative to the robotic arm via base 21. Base 21 may be round, as shown in FIG. 1, or may include any other shape. In one example, the motor 18 may be a component of the system that controls the robotic arm. In this example, the control wires 30 may travel through the housing 20 and through all or a portion of the robotic arm to motor 18, which could be located within the robotic arm or in another location within the robotic device.

Computer Control and Tracking

As noted above, the medical device 10 may be an end effector that may be coupled to the arm of a robotic device, such as the device described in U.S. Pat. No. 8,010,180, titled "Haptic Guidance System and Method" and issued on Aug. 30, 2011, and incorporated herein by reference in its entirety. The robotic arm may include a plurality of links, with each joint between the links providing one or more degrees of freedom. A computer system may control the position of various components of the medical device 10 and of any robotic arm coupled to the medical device 10.

For example, the computer system may be used to control the motion of the control wires 30 and/or the rotation of the cutting tool 50, and may further be used to implement any of the various functions described herein. Motion of the medical device 10 and any other components of the robotic device may be controlled in concert with movements of those devices by an operator. For example, the operator may be able to prompt bending of the flexible tubular member 12 (e.g., by pressing one or more buttons or manually positioning the flexible tubular member). However, working in connection with a navigation system, described below, the computer system may prevent the operator from positioning the flexible tubular member 12 in a manner that would cause the cutting tool 50 to pass certain boundaries designated in a surgical plan, such as a boundary to prevent the cutting tool 50 from cutting too deeply into the patient's bone. The boundaries may be haptic boundaries described in U.S. Pat. No. 8,010,180. To prevent passage of the cutting tool 50 into undesired locations, the computer system may either stop or prompt bending of the tubular member 12.

Similarly, the operator may be able to prompt rotation of the cutting tool 50 (e.g., by pressing a button), but the computer system may be configured to stop rotation of the cutting tool 50 if the operator attempts to position it outside of a designated cutting area (e.g., past a haptic boundary). If the medical device 10 is coupled to the arm of a robotic device, the user may be able to freely move the arm. However, the computer system may be configured to stop movement of the arm and/or override the user's actions if the cutting tool 50 passes over a boundary and into an undesired area.

The computer system may include a processing circuit having a processor and memory. The processor can be implemented as a general purpose processor, an application specific integrated circuit (ASIC), one or more field programmable gate arrays (FPGAs), a group of processing components, or other suitable electronic processing components. The memory (e.g., memory unit, storage device, etc.) may be one or more devices (e.g., RAM, ROM, Flash-memory, hard disk storage, etc.) for storing data and/or computer code for completing or facilitating the various processes described in the present application. The memory may be or include volatile memory or non-volatile memory. The memory may include database components, object code components, script components, or any other type of information structure for supporting the various activities described in the present application. According to an exemplary embodiment, the memory may be communicably connected to the processor and may include computer code for executing one or more processes described herein. The memory may contain a variety of modules, each capable of storing data and/or computer code related to specific types of functions. In one embodiment, the memory contains several modules related to medical procedures, such as a module for controlling the proximal section 22, a module for controlling the distal section 24, and a module for controlling the rotation of flexible shaft 14 and the cutting tool 50.

It should be understood that the computer system need not be contained in a single housing. Rather, components of the computer system may be located in multiple locations, including in one or more remote locations relative to the medical device 10. Components of the computer system, including components of the processor and memory, may be located, for example, in components of a robotic device and system coupled to the medical device 10.

The present disclosure contemplates methods, systems, and program products on any machine-readable media for accomplishing various operations. The machine-readable media may be part of or may interface with the computer system. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The computer system may further include one or more communication interfaces. The communication interfaces can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). For example, communication interfaces can include an Ethernet card and port for sending and receiving data via an Ethernet-based communications link or network. In another example, communication interfaces can include a Wi-Fi transceiver for communication via a wireless communications network. Thus, if the computer system is physically separate from components of the medical device 10, such as the motor 16 or the motor 18, the communication interfaces can enable wireless communications between the computer system and these separate components.

A navigation system 60 may be used to track the position and/or orientation of the cutting tool 50 and other objects in the operating room during image-guided procedures. The navigation system 60 may be any type of navigation system configured to track the position and/or orientation of objects, such as a non-mechanical tracking system, a mechanical tracking system, or any combination of non-mechanical and mechanical systems.

Various types of non-mechanical tracking systems may be used, such as optical and ultrasonic tracking systems. For example, as shown in FIG. 1, the navigation system may include a detection device 62 placed in the operating room to detect visible light. The detection device 62 may be, for example, a MicronTracker (Claron Technology Inc., Toronto, Canada). In an additional or alternative example, the detection device 62 may include a stereo camera pair sensitive to infrared radiation. In yet another example, the detection device 62 may include an ultrasound imaging device or a portion of a fluoroscope (e.g., the X-ray emitter), both of which may allow real-time intraoperative tracking of the medical device 10. In yet another example, the navigation system 60 may include electromagnetic tracking using a transmitter to induce current in electromagnetic sensors embedded or fixed to the tracked objects.

Any example of a navigation system may further include one or more trackable elements 64 secured to objects to be tracked, such as the medical device 10, other components of a robotic device coupled to the medical device 10, or the patient. The trackable elements may be "visible" by the type of detection device being used. Depending on the detection device, the trackable elements may be active (e.g., light-emitting diodes or LEDs) or passive (e.g., reflective spheres, a checkerboard pattern, etc.) and have a unique geometry (e.g., a unique geometric arrangement of the markers) or, in the case of active markers, a unique firing pattern. Other trackable elements may include radio-opaque markers, mechanical features, color-painted elements, or projected optical patterns.

Mechanical tracking systems may additionally or alternatively be used to determine the position and/or orientation of the flexible tubular member 20 and/or the cutting tool 50. In one example, known information about geometry and movement of the joints of the robotic arm and the flexible tubular member 12, for example using sensors in the joints and information about the extent of bending in the proximal and distal sections 22, 24, may be used by the computer system to calculate a position and/or orientation of the cutting tool 50.

In another example, one or more fiber optic shape sensors 66 (FIG. 1) may be coupled to the robotic arm and/or the flexible tubular member 12. The fiber optic shape sensor 66 may travel through a lumen in the wall of the elongated tubular member 12. A fiber optic shape sensor 66 may include one or more optical fibers. The shape (position coordinates and orientation) of an optical fiber may be determined by determining the local fiber bend at multiple sensing points along the optical fiber, as described in U.S. Pat. No. 9,050,131, titled "Fiber Optic Tracking System and Method for Tracking a Substantially Rigid Object," issued Jun. 9, 2015, and hereby incorporated by reference herein in its entirety. In some embodiments, information from a first type of navigation system, such as one that uses a detection device 62 and one or more trackable elements 64, may be combined with information from another type of navigation system, such as the fiber optic shape sensor 66 and the known relationship between the cutting tool 50 and the elongated tubular member 12, to calculate the position and orientation of the cutting tool 50.

The medical device 10 may be calibrated to a computer model to aid in image guidance during surgical procedures. During the calibration process, a 3D camera may capture the shape of the tubular member 12 and movements caused by operation of the control wires 30. The data may then be fitted to a mathematical model in order to create an accurate computerized model of the medical device 10. In one exemplary process, a control wire 30 may be pulled an incremental distance, and the shape of the tubular member 12 may then be measured. A pre-existing model of the tubular member 12 may then be adjusted based on the relationship between the pull distance and the shape of the tubular member 12. This process may be repeated, with the control wire 30 being pulled incrementally, to continually adjust and improve the accuracy of the computerized model.

In operation, the detection device detects positions of the trackable elements, and the computer system, which may include embedded electronics associated with the detection device, may calculate a pose (position and orientation) of the tracked objects to which the trackable elements are fixed, based on the trackable elements' positions, unique geometry, and known geometric relationship to the tracked object.

Calibration of the tubular member 12 and tracking of both the medical device 10, the patient, and other objects in the operating room may allow procedures to be image guided. In an image-guided procedure, a monitor may display a representation of the patient's anatomy and of the tubular member 12 and cutting tool 50. The images may allow a surgeon or other user to see the relationship between the location of the cutting tool 50 and the location of the patient's bone or other anatomy. In some embodiments, the computer system may calculate the distance between the actual position of the cutting tool 50 and the desired position of the cutting tool 50. The computer system may then adjust the position of the medical device 10, automatically or by instructing the surgeon to implement adjustments, to place the cutting tool 50 in the desired position.

Exemplary Applications

The medical device 10 may be used during any procedure that requires modifications to bone. Additionally or alternatively, the medical device 10 may be used to remove softer tissue. The medical device 10 may be used during minimally-invasive procedures through a small incision in the patient's skin. The flexibility of the medical device 10 may allow a surgeon to position the cutting tool 50 in locations that may not be accessible by a straight tool, or in locations in which access by a straight tool would require additional damage to soft tissue. In one example, the medical device 10 may be used during hip and knee arthroplasty procedures. These procedures may require modifications to bone surfaces that may not be easily accessible by a straight tool.

In one specific example, the medical device 10 may be used during femoroacetabular impingement procedures, which may require removal of bone from the acetabular rim or the femoral head and may be performed through a small incision in the patient's skin. Typically, when using straight instruments, a surgeon may have difficulties reaching certain locations within the patient's hip. The flexibility of the medical device 10, however, may allow the surgeon to curve the flexible tubular member 12 around the patient's anatomy to reach hard-to-access locations and effectively reshape the acetabular rim or femoral neck. In another example, the medical device 10 may be used during an endoscopic discectomy. The flexibility of the flexible tubular member 12 may allow the surgeon to more effectively reach desired locations to remove a herniated intervertebral disc.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A system for cutting a bone of a patient, comprising:
a motor;
a rotating shaft drivingly coupled to the motor;
a support tube positioned around the rotating shaft and supporting the rotating shaft at a plurality of locations;
a plurality of steering wires coupled to the support tube; and
a bone cutter at a distal end of the rotating shaft;
wherein the support tube includes a proximal section and a distal section, and the proximal section is independently steerable from the distal section using the plurality of steering wires.

2. The system of claim 1, wherein the support tube has a stiffness of at least 5 N/mm in a bent position.

3. The system of claim 1, wherein the support tube includes a plurality of slots through a wall of the support tube.

4. The system of claim 1, further comprising a navigation system including a detection device and a trackable element.

5. The system of claim 4, wherein the navigation system further includes at least one of a fiber optic shape sensor or an electromagnetic sensor.

6. A medical device, comprising:
a tubular member having a wall and a lumen, wherein the tubular member includes a plurality of slots extending through the wall;
a flexible shaft positioned within the lumen of the tubular member, wherein the flexible shaft is rotatable relative to the tubular member; and
a bone cutter at a distal end of the flexible shaft, wherein the tubular member, in a bent position, has a stiffness of at least 5 N/mm; and
wherein the tubular member includes a proximal section, a distal section, and a plurality of steering wires, and wherein the proximal section is independently steerable from the distal section.

7. The medical device of claim 6, wherein the distal section is steerable by at least four steering wires, with each steering wire including a first section extending along a length of the proximal section and along a length of the distal section and a second section extending along the length of the proximal section and along the length of the distal section, and the proximal section is steerable by at least four additional steering wires, with each of the four additional steering wires including a first section extending along the length of the proximal section and a second section extending along the length of the proximal section.

8. The medical device of claim 6, wherein the medical device includes an enclosed lumen.

9. The medical device of claim 6, wherein the flexible shaft is configured to rotate at a speed of at least 10,000 rpm.

10. A system for cutting a bone of a patient, comprising:
a motor;
a rotating shaft drivingly coupled to the motor;
a support tube positioned around the rotating shaft and supporting the rotating shaft at a plurality of locations;
a plurality of steering wires coupled to the support tube; and
a bone cutter at a distal end of the rotating shaft;
wherein the support tube includes a proximal section and a distal section, and the proximal section is independently steerable from the distal section using the plurality of steering wires; and
wherein the rotating shaft is configured to rotate at a speed of at least 10,000 rpm.

11. The system of claim 10, further comprising a navigation system including a detection device and a trackable element.

12. The system of claim 10, wherein the navigation system further includes at least one of a fiber optic shape sensor or an electromagnetic sensor.

13. The system of claim 10, wherein the support tube has a stiffness of at least 5 N/mm in a bent position.

14. The system of claim 10, wherein the support tube includes a plurality of slots through a wall of the support tube.

* * * * *